United States Patent
Ghelli et al.

(10) Patent No.: US 12,246,120 B2
(45) Date of Patent: Mar. 11, 2025

(54) DEVICE FOR THE MEASUREMENT OF CARBON DIOXIDE IN A WORKING GAS

(71) Applicant: EUROSETS S.R.L., Medolla (IT)

(72) Inventors: Nicola Ghelli, Medolla (IT); Paolo Fontanili, Medolla (IT); Marco Corbelli, Medolla (IT); Michele Bellancini, Medolla (IT); Guido Comai, Medolla (IT)

(73) Assignee: EUROSETS S.R.L., Medolla (IT)

( * ) Notice: Subject to any disclaimer, the term of this patent is extended or adjusted under 35 U.S.C. 154(b) by 1140 days.

(21) Appl. No.: 17/053,921

(22) PCT Filed: May 22, 2019

(86) PCT No.: PCT/IB2019/054221
§ 371 (c)(1),
(2) Date: Nov. 9, 2020

(87) PCT Pub. No.: WO2019/224735
PCT Pub. Date: Nov. 28, 2019

(65) Prior Publication Data
US 2021/0236707 A1    Aug. 5, 2021

(30) Foreign Application Priority Data

May 24, 2018  (IT) .................. 102018000005692

(51) Int. Cl.
*A61M 1/16* (2006.01)
*A61M 1/36* (2006.01)

(52) U.S. Cl.
CPC ........ *A61M 1/1698* (2013.01); *A61M 1/3624* (2013.01); *A61M 2202/0225* (2013.01);
(Continued)

(58) Field of Classification Search
CPC .............. A61M 1/1698; A61M 1/3624; A61M 2202/0225; A61M 2205/3306;
(Continued)

(56) References Cited

U.S. PATENT DOCUMENTS

| | | | | |
|---|---|---|---|---|
| 5,886,348 A | * | 3/1999 | Lessure | G01N 21/3504 250/339.04 |
| 5,932,877 A | * | 8/1999 | Braig | A61B 5/097 250/252.1 |

(Continued)

FOREIGN PATENT DOCUMENTS

WO    WO 2005/102163 A1    11/2005

*Primary Examiner* — Andrew J Mensh
*Assistant Examiner* — Meagan Ngo
(74) *Attorney, Agent, or Firm* — ASLAN LAW, P.C.

(57) ABSTRACT

A device for the measurement of carbon dioxide in a working gas comprises: a tubular body inside which a working gas is conveyed; at least one emitter of an optical signal arranged at the tubular body; at least one receiver of the optical signal arranged at the tubular body on the opposite side of the emitter; heating unit arranged at least one of the emitter and the receiver; wherein the device comprises at least one temperature sensor positioned in the proximity of the heating unit, at least one control unit operatively connected to the emitter, to the receiver, to the heating unit and to the sensor, the control circuit unit comprising correction unit which are configured to correct the value of the optical signal detected by the receiver depending on the temperature measured by the temperature sensor.

14 Claims, 5 Drawing Sheets

(52) U.S. Cl.
CPC ............... *A61M 2205/3306* (2013.01); *A61M 2205/3368* (2013.01); *A61M 2205/36* (2013.01)

(58) Field of Classification Search
CPC ...... A61M 2205/3368; A61M 2205/36; A61M 230/40; A61M 1/36224; A61M 2203/40
See application file for complete search history.

(56) References Cited

U.S. PATENT DOCUMENTS

2008/0097233 A1\* 4/2008 Pedersen ............ A61B 5/14557
600/531
2008/0283062 A1\* 11/2008 Esposito, Jr. ..... A61M 16/0051
128/204.22

\* cited by examiner

DEVICE FOR THE MEASUREMENT OF CARBON DIOXIDE IN A WORKING GAS

CROSS-REFERENCE TO RELATED APPLICATIONS

This application is a National Stage Entry of PCT/IB2019/054221 filed on May 22, 2019. This application claims priority to IT patent application No. 102018000005692 filed on May 24, 2018, and to PCT Application No. PCT/IB2019/054221 filed on May 22, 2019, the entire contents of which are hereby incorporated by reference.

TECHNICAL FIELD

The present invention relates to a device for the measurement of carbon dioxide in a working gas, particularly in the medical field.

BACKGROUND ART

One of the possible medical applications of this type of device is within extracorporeal blood circulation circuits. It is known that during cardiac surgery an extracorporeal blood circulation is established having as its main purpose the perfusion of vital organs, i.e. their supply with oxygenated blood, to ensure the correct function thereof, and for this purpose one of the devices comprised in the extracorporeal circuit consists of an oxygenator in which the blood coming from the venous intake line of the patient is enriched with oxygen before being introduced into the arterial return line to the patient.

In particular, the oxygenator has an inlet channel and an outlet channel of a working gas intended to supply oxygen to the blood and/or to remove carbon dioxide from it.

The amount of carbon dioxide removed by the oxygenator is therefore a parameter of primary importance for assessing the effectiveness and performance of extracorporeal circulation.

For this purpose, or to detect the amount of carbon dioxide removed from the blood coming from the patient, devices are generally used called, in jargon, "capnometers".

Such devices are positioned at the outlet channel of the working gas and comprise an emitter of an optical signal adapted to cross the flow of gas exiting from the oxygenator and a receiver of the optical signal opposite the emitter. Since the carbon dioxide particles absorb energy in the infrared wavelength range, it is easy to see how the signal detected can be traced back to the amount of carbon dioxide present.

Since the possible presence of condensation on optical devices, i.e. on the emitter or on the receiver, can alter the measurement taken, some capnometers of a known type provide for the use of heating means adapted to prevent the formation of condensation.

These devices of known type also have a number of drawbacks, however.

In particular, studies carried out show a decrease in the power of the optical signal emitted as the temperature rises. As can be easily appreciated, this also involves an alteration in the assessment of the amount of carbon dioxide detected.

DESCRIPTION OF THE INVENTION

The main aim of the present invention is to provide a device for the measurement of the amount of carbon dioxide in circuits for the extracorporeal circulation of blood which permits effectively and reliably detecting the amount of carbon dioxide removed from the blood.

Within this aim, one object of the present invention is to perform continuous detection over time.

Another object of the present invention is to provide a device for the measurement of carbon dioxide in circuits for the extracorporeal circulation of blood that allows overcoming the mentioned drawbacks of the prior art in a simple, rational, easy, effective to use and cost effective solution.

The aforementioned objects are achieved by the present device for the measurement of carbon dioxide in a working gas according to claim 1.

BRIEF DESCRIPTION OF THE DRAWINGS

Other characteristics and advantages of the present invention will be more evident from the description of a preferred, but not exclusive, embodiment of a device for the measurement of carbon dioxide in a working gas, illustrated by way of an indicative, yet non-limiting example, in the attached tables of drawings in which.

EMBODIMENTS OF THE INVENTION

Figure 1:
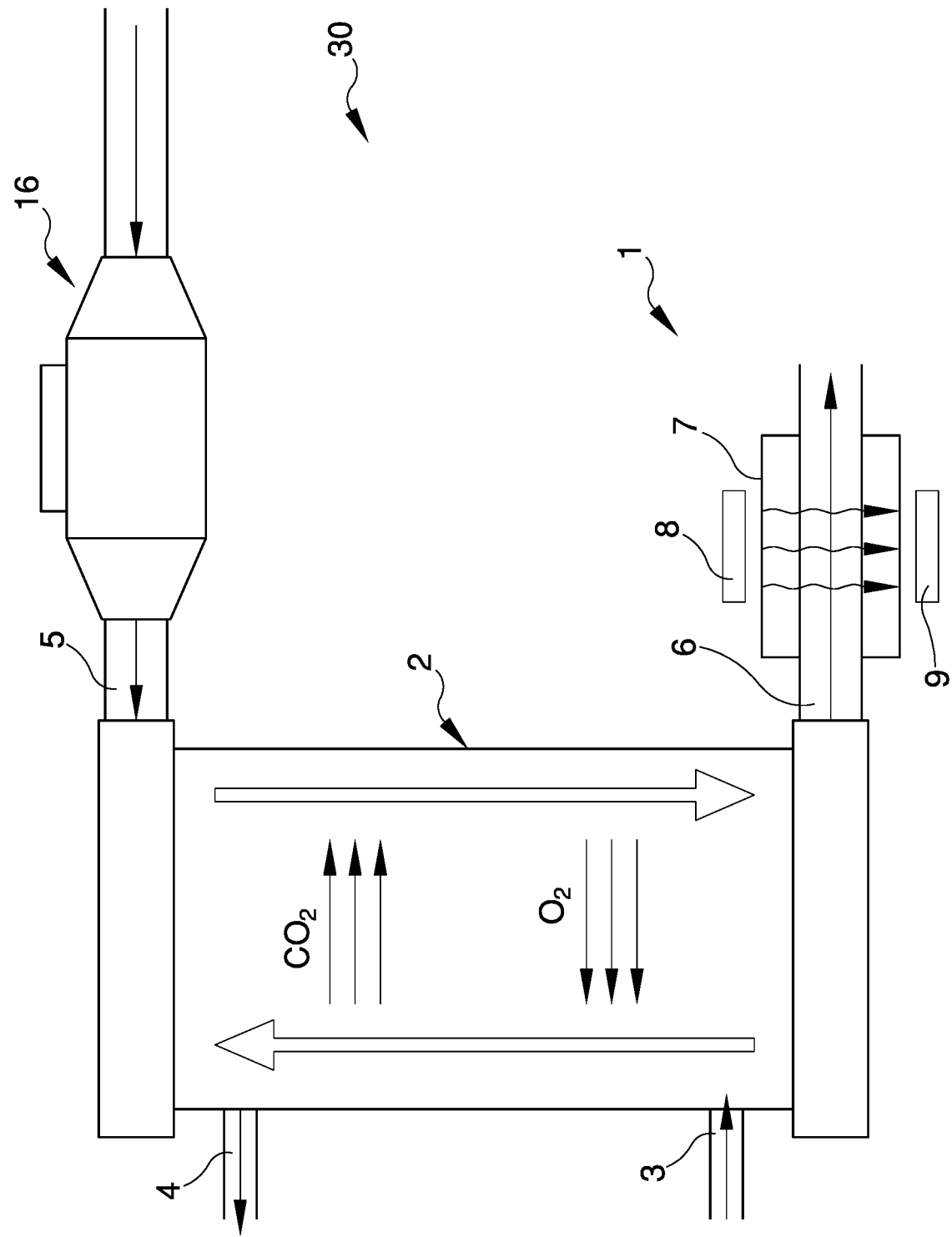
FIG. 1 is a schematic representation of a circuit for the extracorporeal circulation according to the invention.

With particular reference to these illustrations, reference numeral 1 globally indicates a device for the measurement of carbon dioxide in a working gas.

The device 1 comprises a tubular body 7, inside which a working gas is conveyed, e.g. of the type of a gas mixture, at least one emitter 8 of an optical signal arranged at the tubular body 7 and at least one receiver 9 of the optical signal arranged at the tubular body 7 on the opposite side of the emitter 8. The tubular body 7 is arranged within a box body 20a, 20b. In the embodiment shown in FIG. 2, the box body 20a, 20b is composed of the portions 20a and 20b, which are connected together by means of threaded members 21.

Appropriately, the emitter 8 and the receiver 9 are of the type of infrared photodiodes. The emitter 8 and the receiver 9 are composed e.g. of diodes of the InAsSb/InAs type.

More particularly, the tubular body 7 is of the type of a "cuvette" made of transparent material.

The device 1 then comprises heating means 10, 11 arranged at at least one of the emitter 8 and the receiver 9.

The heating means 10, 11 comprise at least first heating means 10 arranged at the emitter 8.

Preferably, the heating means 10, 11 also comprise second heating means 11 arranged at the receiver 9.

Advantageously, the heating means 10, 11 are composed of a relative heating element provided with at least one through hole 12 which faces onto the tubular body 7 and inside which the corresponding emitter 8 or the receiver 9 is inserted. The heating element 10, 11 is provided with a relative resistance 19 connected to power supply means. The heating element 10, 11 is suitably made of a heat conducting material, e.g. a metal material. The heating means therefore comprise two heating elements 10, 11, arranged on opposite sides with respect to the tubular body 7 and facing each other, of which the first heating element 10 has a relative hole 12 in which the emitter 8 is inserted and the second heating element 11 has a relative hole 12 in which the receiver 9 is inserted.

The heating means 10, 11 are also located inside the box body 20a, 20b. Between the box body 20a, 20b and the tubular body 7, and between the latter and the heating means 10, 11, are suitably interposed sealing means 22, e.g., of the O-ring type.

Figure 2:
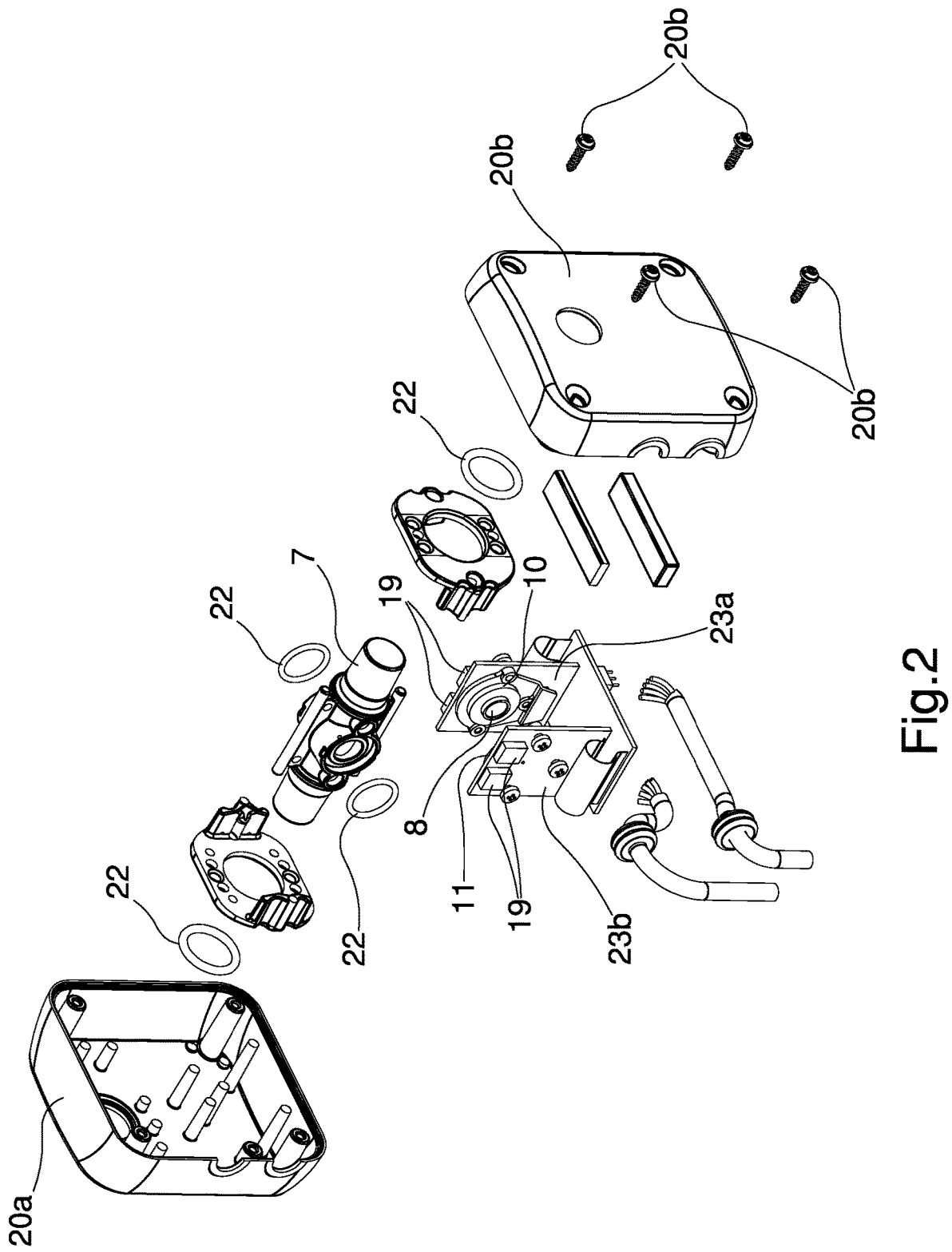
FIG. 2 is an axonometric exploded view of a device for the measurement of carbon dioxide according to the invention.
Figure 3:
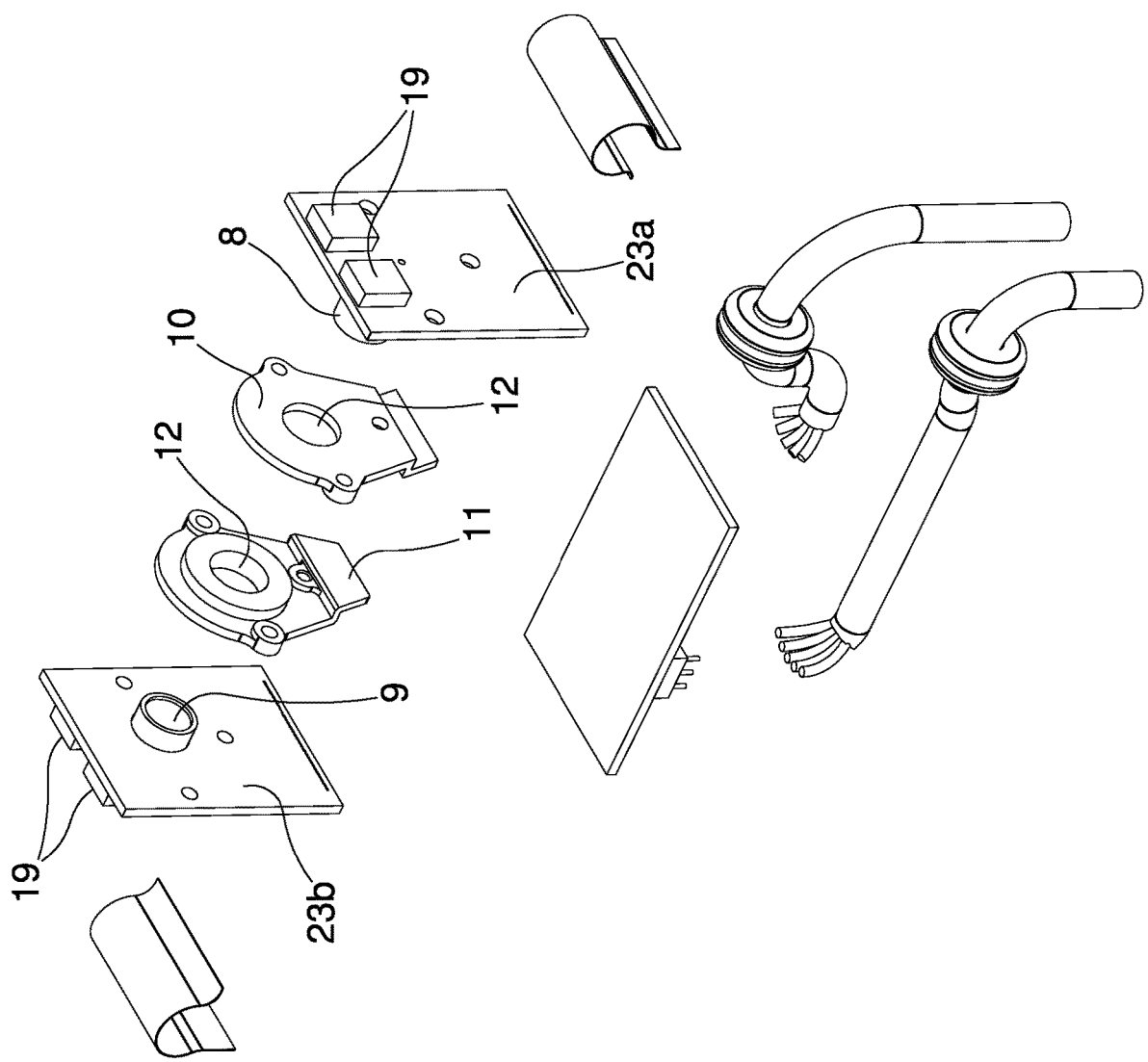
FIG. 3 is an axonometric view of a portion of the device of FIG. 2.
Figure 4:
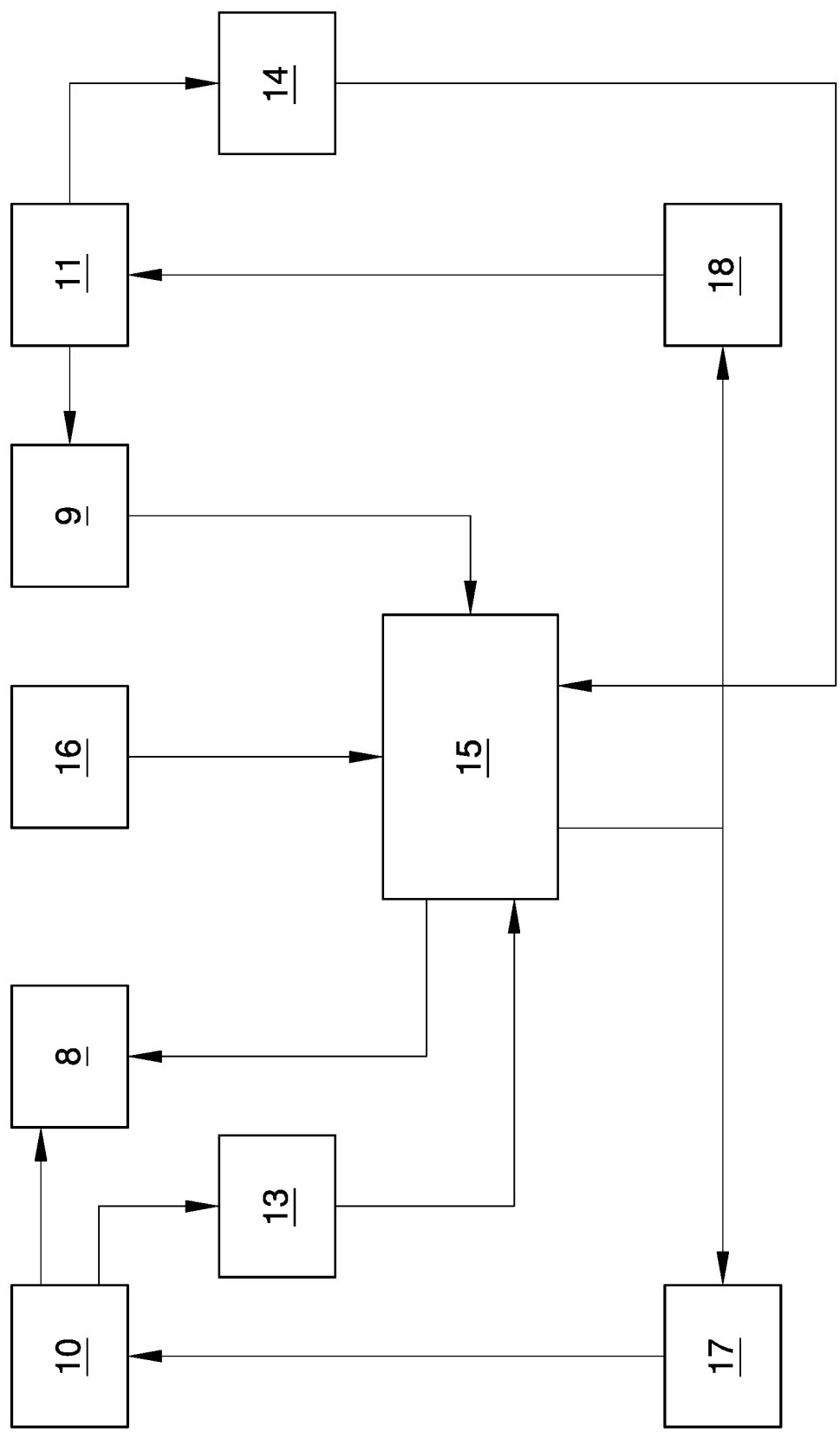
FIG. 4 is a schematic representation of the control logics of a device according to the invention.

In the embodiment shown in FIGS. 2 and 3, the heating means 10, 11 are fixed to relevant support elements 23a, 23b arranged inside the box body 20a, 20b. According to the invention, the device 1 comprises at least one temperature sensor 13, 14 positioned in the proximity of the heating means 10, 11 and at least one control unit 15 operatively connected to the emitter 8, to the receiver 9, to the heating means 10, 11 and to the sensor 13, 14.

The device 1 comprises at least a first temperature sensor 13 arranged in the proximity of the first heating means 10. More in particular, the first sensor 13 is associated with the first heating element 10.

The device 1 preferably also comprises a second temperature sensor 14 arranged in the proximity of the second heating means 11. More in particular, the second sensor 14 is associated with the second heating element 11.

The control unit 15 comprises correction means which are configured to correct the value of the optical signal detected by the receiver 9 depending on the temperature measured by at least one of the sensors 13, 14.

Advantageously, the control unit 15 comprises first means for calculating a filtered optical signal Sf, corresponding to the average of the signals received by the receiver 9 in a first dynamic time range, second means for calculating a filtered temperature Tf, corresponding to the average temperature measured by the temperature sensor 13, 14 in a second dynamic time range, and third means for calculating a corrected optical signal Sc according to the following formula:

$$Sc = Sf + (Tr - Tf) \times C$$

where Sf corresponds to the filtered optical signal, Tr corresponds to a pre-settable reference temperature, Tf corresponds to the filtered temperature and C corresponds to a pre-settable coefficient.

The wording "dynamic time range" means a time range of predefined length that moves in time, i.e. the time range within which the average value of the corresponding signal is calculated moves with the passing of time.

The use of dynamic time ranges to calculate the filtered optical signal and the filtered temperature makes it possible to correct any temperature fluctuations due to the construction limits of the heating means and the inaccuracy in the temperature measurement due to the distance between the sensor 13, 14 and the relative optical device 8, 9.

Preferably, the filtered temperature Tf corresponds to the average temperature measured by the first temperature sensor 13 in the second dynamic time range. The reference temperature Tr is preferably between 41° C. and 43° C., e.g. equal to 42° C.

The coefficient C is preferably between 81 and 81.5, e.g. equal to 81.2.

Appropriately, the device 1 comprises control means 17, 18 for controlling the temperature of the heating means 10, 11. The control means 17, 18 are configured to keep the temperature of the heating means 10, 11 at a substantially predefined value. This predefined temperature value can, for example, be set by an operator using hardware means.

The control means 17, 18 are configured to raise the temperature of the heating means 10, 11 until the pre-set temperature is reached. Once the pre-set temperature has been exceeded, the control means 17, 18 interrupt the current flow on the relative resistances 19. When the temperature of the heating means 10, 11 drops below the pre-set temperature, the control means 17, 18 again start the flow of current onto the resistances 19. The control means 17, 18 are operationally connected to temperature sensors, separate from the sensors 13, 14 and not visible in detail in the illustrations, arranged in the proximity of the heating means 10, 11.

More in detail, the control means 17, 18 comprise first control means 17 of the first heating means 10 and second control means 18 of the second heating means 11.

In the embodiment of FIG. 1, the device 1 is inserted in a circuit for extracorporeal blood circulation, identified with the reference numeral 30, comprising a blood oxygenator 2 provided with at least one inlet port 3 of the blood to be oxygenated, at least one outlet port 4 of the oxygenated blood, at least one inlet channel 5 and at least one outlet channel 6 of a working gas, e.g. air or oxygen, intended to supply oxygen to the blood and/or to remove carbon dioxide from it. More particularly, the tubular body 7 is connected to the outlet channel 6.

Advantageously, the circuit 30 also comprises measuring means 16 of the working gas flow rate, e.g. of the type of a fluxmeter, associated with the inlet channel 5.

In more detail, the measuring means 16 are operatively connected to the control unit 15, which comprises fourth means for calculating the percentage of carbon dioxide removed from the blood depending on the measured flow rate of working gas and on the corrected optical signal Sc.

Figure 5:
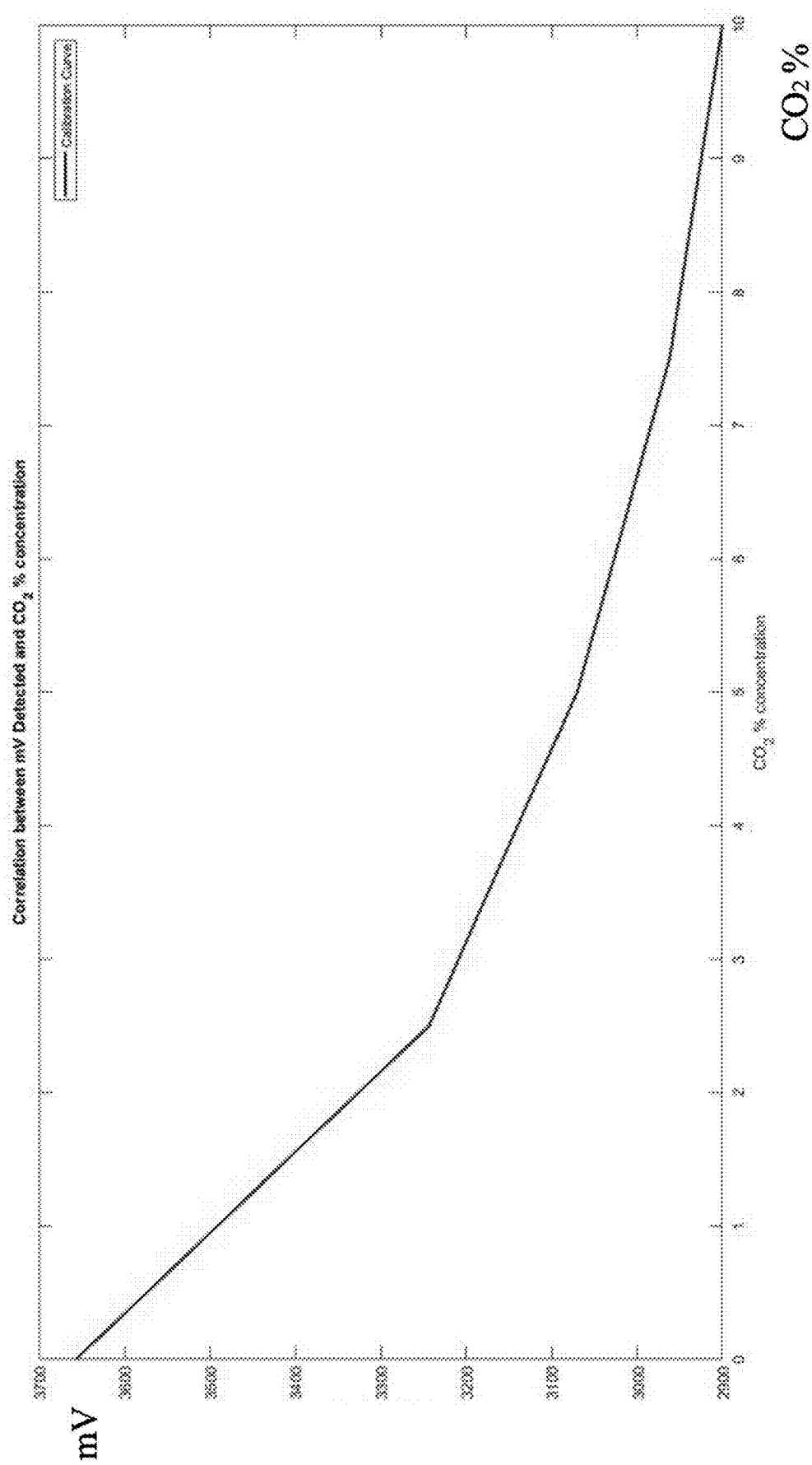
FIG. 5 is a graph illustrating the relationship between the filtered optical signal Sf and the amount of carbon dioxide present is of the linear type.

The relationship between the filtered optical signal Sf and the amount of carbon dioxide present is of the linear type, and is represented by the graph with broken lines as shown in FIG. 5, which shows the concentration of carbon dioxide in the abscissa and the power of the electrical signal received expressed in mV in the ordinate.

The first, second, third and fourth means of calculation are implemented using dedicated software and/or hardware.

The functioning of the device in the execution of the method according to the invention is as follows.

First of all, it is necessary to provide at least the emitter 8 and the receiver 9 with an optical signal.

More particularly, a device is provided according to what is described above and therefore provided with a tubular body 7 which can be connected to the outlet channel 6 of the oxygenator 2, from opposite parts of which the emitter 8 and the receiver 9 are positioned.

Once the extracorporeal blood circulation is started, by means of the emitter 8, an optical signal is emitted adapted to cross the working gas coming out of the oxygenator 2 and the signal itself is received by means of the receiver 9.

The method referred to in the present invention also provides the heating of at least one of the emitter 8 and the receiver 9, in order to avoid the formation of condensation on these, the detection of the temperature of the heated emitter 8 and/or receiver 9, and the correction of the optical signal depending on the detected temperature.

Advantageously, the correction phase comprises in turn the following steps of:
- calculation of the filtered optical signal Sf corresponding to the average of the signals received by the receiver 9 in a first dynamic time range;
- calculation of the filtered temperature Tf, corresponding to the average temperature measured of the emitter 8 and/or of the receiver 9 in a second dynamic time range;
- set up of a reference temperature Tr;
- set up of a constant value C;
- calculation of the corrected optical signal Sc according to the formula:

$$Sc=Sf+(Tr-Tf)\times C$$

where Sf corresponds to the filtered optical signal, Tr corresponds to the reference temperature, Tf corresponds to the filtered temperature and C corresponds to the constant value.

Preferably, the filtered temperature Tf corresponds to the average temperature measured of the emitter 8.

The calculated optical signal Sc is then processed, by comparison with the emitted optical signal, to determine the amount of carbon dioxide present in the working gas.

The flow rate of the working gas entering the oxygenator is also measured and the percentage of carbon dioxide coming out of the oxygenator is calculated.

It has, in practice, been ascertained that the described invention achieves the intended objects, and, in particular, the fact is underlined that the device for measuring the carbon dioxide to which this invention refers permits obtaining a signal, relating to the amount of carbon dioxide present in the working gas coming out of the oxygenator of an extracorporeal circuit, which takes into consideration the effect of the heating applied to the relative optical devices (emitter and receiver).

In particular, the device according to the invention allows limiting the temperature detection error of the optical devices, attributable both to the oscillation of the temperature of the heating means, and to the fact that the temperature is detected at the heating means themselves and not at the optical devices.

The invention claimed is:

1. A device for measurement of carbon dioxide in a working gas, the device comprising:
    a tubular body inside which the working gas is conveyed;
    at least one emitter of an optical signal arranged at said tubular body;
    at least one receiver of said optical signal arranged at said tubular body on a side of said emitter;
    heating means located to be arranged either at said at least one emitter or at said at least one receiver;
    at least one temperature sensor positioned in a proximity of said heating means; and
    at least one control unit operatively connected to said at least one emitter, to said at least one receiver, to said heating means and to said at least one temperature sensor, wherein
    said at least one control unit comprising correction means which are configured to correct a value of the optical signal detected by said at least one receiver based on a temperature measured by said at least one temperature sensor, and
    said correction means comprise first means for calculating a filtered optical signal (Sf), corresponding to the average of the signals received by said at least one receiver in a first dynamic time range, second means for calculating a filtered temperature (Tf), corresponding to the average temperature measured by said at least one temperature sensor in a second dynamic time range, and third means for calculating a corrected optical signal (Sc) according to the following formula:

$$Sc=Sf+(Tr-Tf)\times C$$

where Sf corresponds to said filtered optical signal, Tr corresponds to a pre-settable reference temperature, Tf corresponds to said filtered temperature and C corresponds to a pre-settable coefficient.

2. The device according to claim 1, wherein said heating means comprises at least first heating means arranged at said at least one emitter, wherein at least a first temperature sensor arranged in the proximity of said first heating means, and wherein said filtered temperature (Tf) corresponds to the average temperature measured by said first temperature sensor in said second dynamic time range.

3. The device according to claim 2, wherein said heating means comprise second heating means arranged at said at least one receiver and wherein at least a second temperature sensor is arranged in the proximity of said second heating means.

4. The device according to claim 2, wherein said heating means comprise at least a relative heating element provided with at least one through hole which faces onto said tubular body and inside which said at least one emitter or said at least one receiver is inserted.

5. The device according to claim 4, wherein said at least one temperature sensor is associated with said heating element.

6. The device according to claim 1, wherein said reference temperature (Tr) is between 41° C. and 43° C.

7. The device according to claim 1, wherein the value of said pre-settable coefficient (C) is between 81 and 81.5.

8. The device according to claim 1, wherein said at least one emitter and at least one receiver are of the type of infrared photodiodes.

9. A circuit for extracorporeal blood circulation, said circuit comprising:
    a blood oxygenator provided with at least one inlet port of blood to be oxygenated, at least one outlet port of the oxygenated blood, at least one inlet channel and at least one outlet channel of a working gas intended to supply oxygen to the blood and/or to remove carbon dioxide the blood;
    a device for the measurement of carbon dioxide according to claim 1, wherein said tubular body is connected to said outlet channel of the working gas.

10. The circuit according to claim 9, wherein said circuit comprises measuring means of the working gas flow rate which are associated with said inlet channel.

11. The circuit according to claim 10, wherein said measuring means are operatively connected to said at least one control unit, said at least one control unit comprising fourth means for calculating the percentage of carbon dioxide removed from the blood depending on the measured flow rate of working gas and on said corrected optical signal (Sc).

12. A method for the measurement of carbon dioxide in a working gas, said method comprising:
    supply of at least one tubular body inside which the working gas is conveyed;
    supply of at least one emitter of an optical signal and at least one receiver of said optical signal;
    emission of an optical signal passing through said at least one tubular body;

reception of said optical signal by means of said at least one receiver;

heating of at least one of said at least one emitter and said at least one receiver;

measurement of a temperature of said at least one heated emitter and/or of said at least one heated receiver;

correction of said received optical signal depending on said measured temperature in order to obtain a corrected optical signal (Sc);

processing of said corrected optical signal (Sc) to determine an amount of carbon dioxide present in the working gas which passes through said at least one tubular body;

calculation of a filtered optical signal (Sf) corresponding to the average of the optical signals received by said at least one receiver in a first dynamic time range;

calculation of a filtered temperature (Tf), corresponding to the average of the temperature measured in a second dynamic time range;

set up of a reference temperature (Tr);

set up of a predefined coefficient (C); and calculation of said corrected optical signal (Sc) according to the formula:

$$Sc = Sf + (Tr - Tf) \times C$$

where Sf corresponds to said filtered optical signal, Tr corresponds to said reference temperature, Tf corresponds to said filtered temperature and C corresponds to said predefined coefficient.

13. The method according to claim 12, wherein said measured temperature is relative to the temperature of said at least one emitter.

14. The method according to claim 12, said method further comprises:

supply of at least one circuit for extracorporeal blood circulation comprising a blood oxygenator provided with at least one inlet port of the blood to be oxygenated, at least one outlet port of the oxygenated blood, at least one inlet channel and at least one outlet channel of the working gas, the working gas being intended to supply oxygen to the blood and/or to remove carbon dioxide from the blood; and connection of said at least one tubular body to said at least one outlet channel.

* * * * *